US007070917B1

(12) United States Patent
Christensen et al.

(10) Patent No.: US 7,070,917 B1
(45) Date of Patent: Jul. 4, 2006

(54) DETERMINATION OF SPERM CONCENTRATION AND VIABILITY FOR ARTIFICIAL INSEMINATION

(76) Inventors: Preben Christensen, Dalgas Boulevard 89, 1.th., DK-2000, Frederiksberg (DK); Jens Peter Stenvang, Bransbjergvej 119, 2600 Glostrup (DK)

( * ) Notice: Subject to any disclaimer, the term of this patent is extended or adjusted under 35 U.S.C. 154(b) by 0 days.

(21) Appl. No.: 09/914,765

(22) PCT Filed: Mar. 6, 2000

(86) PCT No.: PCT/DK00/00092

§ 371 (c)(1),
(2), (4) Date: Nov. 8, 2001

(87) PCT Pub. No.: WO00/54026

PCT Pub. Date: Sep. 14, 2000

(30) Foreign Application Priority Data

Mar. 6, 2000 (DK) ................................ 1999 00317

(51) Int. Cl.
*A01N 1/02* (2006.01)
(52) U.S. Cl. ........................................................ 435/2
(58) Field of Classification Search ..................... 435/2
See application file for complete search history.

(56) References Cited

U.S. PATENT DOCUMENTS

| 4,559,309 A | 12/1985 | Evenson et al. |
| 4,751,188 A | 6/1988 | Valet |
| 4,880,732 A | 11/1989 | Resli et al. |
| 5,229,265 A | 7/1993 | Tometsko |
| 5,436,134 A | 7/1995 | Haugland et al. |
| 5,691,133 A | 11/1997 | Critser et al. |
| 5,812,312 A | 9/1998 | Lorincz |
| 5,866,354 A | 2/1999 | Froman |

FOREIGN PATENT DOCUMENTS

| EP | 0586183 | 3/1994 |
| GB | 2145112 | 3/1985 |
| GB | 2214518 | 9/1989 |
| WO | 93/16385 | 8/1993 |
| WO | 95/29983 | 11/1995 |

OTHER PUBLICATIONS

Live/Dead Sperm Viability Kit, Molecular Probes revised Aug. 11, 1999.*
Garner et al., Viability Assessment of Mammalian Sperm using SYBR-14 and Propidium Iodide, Biology of Reproduction 53 (2): 276-84 (1995).*
Clay et al., "Effect of Dilution, Polyvinyl Alcohol (PVA) and bovine serum albumin on Stallion Spermatozoal Motility", Int. Congr. Anim. Reprod. Artif. Insemin., 10ht (1984), vol. 2, No. 187.*

Sexton, "Relationship of the Number of Spermatoza Inseminated to Fertility of Turkey Semen Stored 6 Hours at 5 Celsius", Br. Poult. Sci. 27 (2) : 237-246 (1986).*
Januskauskas et al., "Influence of Sperm Number per Straw on the Post-Thaw Sperm Viability and Fertility of Swedish Red and White A.I. Bulls", Acta Veterinaria Scandinavica 37 (4) : 461-470 (1996).*
Belorkar et al., "Studies on Seminal and Mensurational Characteristics of Spermatozoa and Their Interrelationships with Freezability and Fertility in Crossbred Bulls", PKV Res. J. 14 (2) : 165-173 (1991).*
Bostofte et al., "Human Semen Quality Classification and Pregnancies Obtained During a 20 Year Follow-up Period", Gertil. Steril. 36 (10 :84-87 (1981).*
Juonala et al., "Three Floursecence Methods for Assessing Boar Sperm Viability" , Reproduction in Domestic Animals 34 (2) : 83-87 (1991).*
Viudes-De-Castro et al., "Effect of Sperm Count on the Fertility and Prolificity Rates of Meat Rabbits", Animal Reproduction Science 46 (3-4) : 313-319 (1997).*
Patent Abstract of Japan, vol. 97, No. 4; Abstract of Japanese Patent Publication No. 08332098, published Dec. 17, 1996 (Appl. No. 07161538 Abstract in English language).
Donoghue AM, Garner DL, Donoghue DJ, Johnson LA, 1995: Viability Assesment of Turkey Sperm Using Flourescent Staining and Flow Cytometry. Poultry Sci, 74:1191-1200.
Donoghue AM, Thistlethwaite D, Donoghue DJ, Kirby JD, 1996: A New Method for Rapid Determination of Sperm Concentration in Turkey Semen. Poultry Sci., 75:785-789.
Dumont P, Coupet H, Gary F, 1996: Some aspects of evaluation of semen quality and processing in France. Proc. 8th European AI-Vets meeting.
Evenson DP, Parks JE, Kaproth MT, Jost LK, 1993: Rapid Determination on Sperm Cell Concentration in Bovine Semen by Flow Cytometry. J Dairy Sci 76:86-94.

(Continued)

*Primary Examiner*—Sandra E. Saucier
(74) *Attorney, Agent, or Firm*—Hunton & Williams

(57) ABSTRACT

A method for the simultaneous determination of the total concentration of sperm cells and the proportion of live sperm cells in a semen sample is provided. By selective staining of live, dead and/or dying sperm cells, for example using one or more fluorochromes, the detection means can distinguish between live, dead and/or dying sperm cells, for example by detection of the fluorescent response from the sperm cells. The selective staining may be performed at room temperature and in concentrations below standard concentrations. The determination may be performed by selective counting of cells of each fluorescent quality for example by using a flow cytometer having internal concentration standard means. Furthermore, the likelihood of fertilizing a female animal with an insemination dose, taken from a semen sample having a known total concentration of sperm cells and a known proportion of live sperm cells, is predicted on the basis of the thus determined total concentration of sperm cells and the proportion of live sperm cells.

38 Claims, 7 Drawing Sheets

OTHER PUBLICATIONS

Fenton SE, Ax RL, Cowan CM, Coyle T, Gilbert GR, Lenz RW: Validation and Application of an Assay of Deocyribonucleic Acid to Estimate Concentrations of Bull Sperm. J. Dairy Sci., 73:3118-3125 (1990).

Foote RH, 1972: How to Measure Sperm Cell Concentration by Turbidity (Optical Density). Proceedings 4th Techn. Conf. on Anim. Reprod. and AI, NAAB, pp. 2-6.

Garner DL, Johnson LA, Yue ST, Roth BL, Haugland RP, 1994: Dual DNA Staining Assessment of Bovine Sperm Viability Using SYBR-14 and Propidium Iodide. J Androl,15:620-629.

Garner DL and Johnson LA, 1995: Viability Assessment of Mammalian Sperm Using SYBR-14 and Propidium Iodide. Biol Reprod, 53:276-84.

Garner DL, Dobrinsky JR, Welch GR, Johnson LA, 1996a: Porcine Sperm Viability, Oocyte Fertilization and Embryo Development after Staining Spermatozoa with SYBR-14. Theriogenology, 45:1103-1113.

Garner DL, Johnson LA, Allen CH, Palencia DD, Chambers CS, 1996b: Comparison of Seminal Quality in Holstein Bulls as Yearlings and as Mature Sires. Theriogenology, 45:923-934.

Garner DL, Thomas CA, Joerg HW, DeJarnette JM, Marshall CE, 1997a: Fluorometric Assessments of Mitochondrial Function and Viability in Cryopreserved Bovine Spermatozoa. Biol Reprod, 57:1401-1406.

Garner DL, Thomas CA, Allen CH, 1997b: Effect of Semen Dilution on Bovine Sperm Viability as Determined by Dual-DNA Staining and Flow Cytometry. J Androl, 18:324-331.

Garner DL, Thomas CA, Allen CH, Sasser RG, 1997c: Effect of Cryopreservation on Bovine Sperm Viability as Determined by Dual DNA Staining. Reprod. Domest. Anim, 32:279-283, Maxwell WM and Johnson LA, 1997: Chlortetracycline Analysis of Boar Spermatozoa After Incubation, Flow Cytometric Sorting, Cooling, or Cryoperservation. Mol Reprod Dev, 46:408-418.

Maxwell WM, Welch GR, Johnson LA, 1997: Viability and Membrane Integrity of Spermatozoa *after Dilution and Flow Cytometric Sorting in the Presence or Absence of Seminal Plasma*. Reprod. Fertil. Dev, 8:1165-78.

Parks JE, Ehrenwald E, Foote RH, 1985: Counting mammalian spermatozoa in biological fluids containing particulate matter. J. Dairy Sci., 68:2329.

Penfold LM, Garner DL, Donoghue AM, Johnson LA, 1997: Comparative Viability of Bovine Sperm Frozen on a Cryomicroscope or in Straws. Theriogenology, 47:521-530.

Songsasen N, Betteridge KJ, Leibo SP, 1997: Birth of Live Mice Resulting from Oocytes Fertilized In Vitro with Cryopreserved Spermatozoa. Biol Reprod, 56:143-152.

Szollosi J, Takacs T, Balazs M, Gaspar R, Matyus L, Szabo G, Tron L, Resli I, Dajanovich S,1986: Flow-cytometric evaluation of bull semen. 1. Objective determination of sperm cell counts in diluted semen samples. Magyar Allatorvosok Lapja, 41:459-463.

Takacs T, Szollosi J, Balazs M, Gaspar R, Matyus L, Sazabo G, Tron L, Resli I, Damjanovich S: Flow cytometric determination of the sperm cell number in diluted bull semen samples by DNA staining method. Acta. Bichim. Biophys. Hung., 22:45-57 (1987).

Takizawa S, Katoh C, Fukatsu N, Horii I, 1994: Evaluation of rat sperm viability and number by flow cytometry. Teratology, 50:40B.

Takizawa S, Katoh C, Fukatsu N, Horii I, 1995: Flow Cytometric Analysis for the Evaluation of the Rat Sperm Viability and Number in the Male Reproductive Tocicity Studies. Cong. Anom, 35:177-187.

Takizawa S, Katoh C, Inomata A, Horii I, 1998: Flow cytometric analysis for sperm viability and counts in rats treated with trimethylphosphate or pyridoxine. J. Toxicol. Sci. 23:15-23.

Thomas CA, Garner DL, DeJarnette JM, Marshall CE, 1997: Fluorometric Assesments of Acrosomal Integrity and Viability in Cryopreserved Bovine Spermatozoa. Reprod. Biol, 56:991-998.

Thomas CA, Garner DL, DeJarnette JM, Marshall CE, 1998: Effect of Cryopreservation on Bovine Sperm Organelle Function and Viability as Determined by Flow Cytometry. Biol Reprod 58:786-793.

Vetter CM, Miller JE, Crawford LM, Armstrong MJ, Clair JH, Conner MW, Wise DL, Skopek TR, 1998: Comparison of motility and membrane integrity to assess rat sperm viability. Reprod Toxicol, 12:105-114.

Woelders H, 1990: Overview of in vitro methods for evaluation of semen quality. Boar Semen Preservation II, Reprod. Domest. Anim, Suppl 1: 145-164.

Yamamoto T, Mori S, Yoneyama M, Imanishi M, Takeuchi M, 1996: Estimation of rat sperm with flow cytometer (FCM): simultaneous analysis of sperm number and sperm viability. Teratology, 54:38A.

Chalah T, Brillard JP, 1998: Comparison of assessment of fowl sperm viability by eosin-nigrosin and dual flourescence (SYBR-14/PI). Theriogenology, 50:487-493.

Amann RP, 1989: Can the fertility potential of a seminal sample be predicted accureately? J Androl 10, 89-98.

Budworth PR, Amann RP, Chapman PL, 1988: Relationships between computerized measurement of motion of frozen-thawed bull spermatozoa and fertility. J. Androl 9, 41-54.

Christensen P, Stryhn H, 1997: Time-dependent bias in the assessment of bull semen by computer-aided sperm analysis. Biol Reprod 56, Suppl 1, 173.

Christensen P, Brockhoff PB, Lehn-Jensen H ,1999: The Relationship between Semen Quality and the Nonreturn Rate of bulls. Reprod Dom Anim 34, 503-507.

Barth AD, Oko RJ, 1989: Abnormal Morphology of Bovine Spermatozoa. 1st edition, Iowa State University Press, pp. 160-163.

Christensen, P., et al. 2004. A flow cytometric method for rapid determination of sperm concentration and viability in mammalian and avian semen. J. Androl. 2004, 25:255-264.

Christensen, P. et al. 2005. Relationship Between Sperm Viability as Determined by Flow Cytometry and Nonreturn Rate of Dairy Bulls. Journal of Andrology, vol. 26, No. 1, Jan./Feb. 2005.

Den Daas, J.H.G. et al. 1998. The relationship between the number of spermatozoa inseminated and the reproductive efficiency of individual dairy bulls. J. Dairy Sci. 81, 1714-1723.

Evenson et al., "*Simultaneous Measurement by Flow Cytometry of Sperm Cell Viability and Mitochondrial Membrane Potential Related to Cell Motility,*" Letters to the Editor, The Journal of Histochemistry and Cytochemistry, vol. 30, No. 3, pp. 279-280, 1982.

Arefyev et al., "*Microparticles Laser Flow Scintillator-Analyzer Used to Assay Spermatozoa in Ejaculate,*" Lab Delo, 1987; (1) 22-25, English Abstract.

\* cited by examiner

DETERMINATION OF SPERM CONCENTRATION AND VIABILITY FOR ARTIFICIAL INSEMINATION

This is a 371 filing of PCT/DK00/00092 filed Mar. 6, 2000.

TECHNICAL FIELD

The invention relates to the simultaneous determination of sperm concentration and live sperm cells in a semen sample.

BACKGROUND OF THE INVENTION

Accurate and precise determination of viable sperm concentration is an important issue for the Artificial Insemination (AI) industry since it provides assurance to the studs and customers that the insemination doses contain the sperm numbers indicated. This is especially important in relation to exportation of semen from domesticated animal species (Foote, 1972; Fenton et al., 1990; Woelders 1990; Evenson et al., 1993; Donoghue et al., 1996).

It is known in the art to use counting chambers such as Makler™ (Sefi Medical, Haifa, Israel) or hemacytometers for routine sperm counts. However, multiple measurements are required to achieve an acceptable precision and accuracy. This procedure is time consuming and makes the counting chambers slow in use. Single hemacytometer counts are not highly accurate because of inherent errors in the technique, such as obtaining a subsample representative of the semen sample, etc, and furthermore, the process is highly dependant upon operator skills.

A technique widely used by the artificial insemination industry to determine sperm cell concentration is based on spectrophotometric measurement of turbidity (Woelders 1990; Evenson et al., 1993). However, this method requires a calibration of the spectrophotometer which is repeated at regular intervals since the performance of the instrument will vary over time, whereby this method is only as accurate as the calibration method. The calibration is most often based on one of the counting chambers mentioned above, whereby the spectrophotometer method is only as accurate as the counting chamber methods mentioned above.

A further disadvantage of the spectrophotometer method is that debris, such as gel-particles in boar semen, increases the semen turbidity whereby inaccuracies are introduced in the method since distinguishing debris from semen is very difficult (Woelders 1990) and the method is used only extensively because of the rapidity of the method and the fact that no other method works in a satisfactory manner for these species.

Semen from species without large gel-particles in the semen may be analyzed on electronic counters wherein particles having a specific particle size are counted (Parks et al., 1985). However, electronic counters are not capable of distinguishing semen cells from debris having a particle size corresponding to the particle size of the semen cells. Since semen from most species contains a high number of particles having a size corresponding to the size of spermatozoa (i.e. cytoplasmic droplets) the resulting counts for individual ejaculates can be highly inaccurate (Parks et al., 1985).

The evaluation of semen quality in artificial insemination stations as well as in laboratories for human semen and the evaluation of semen quality for semen from laboratory animals is normally based on an evaluation of sperm motility using a phase contrast microscope with a heated stage (Woelders, 1990). Although this procedure is valuable to ensure that semen of very poor quality is excluded from artificial insemination, the method does not have a high precision or accuracy. Furthermore, the method is highly dependent on operator skills and large variations are observed in the results obtained by different operators.

It is also known in the art to use flow cytometers for a characterisation of the sperm (Szollosi et al., 1986; Takacs et al., 1987; Evenson et al., 1993). In the methods disclosed, the sperm has been killed and stained with propidium iodide, PI, to measure sperm concentration. Thereby, only sperm concentration is found. It is a disadvantage of the method that no indication of the amount of live sperm cells is provided.

In another method, only the dead sperm cells are stained by propidium iodide, whereafter light scattered from the unstained particles (including live sperm) is detected. This method has been used by Takizawa et al. (1994, 1995 and 1998) as well as by Yamamoto et al. (1996). In this method, there is no discrimination between live spermatozoa and debris in the semen. Thereby, gel-particles, cytoplasmic droplets, debris and bacteria are likely to be included in the sperm count according to this method, thereby inflating the value of both the measured concentration and detected viability.

It is further known in the art to stain sperm cells using a fluorescent dye called SYBR-14 and propidium iodide, PI, (LIVE/DEAD® Sperm Viability Kit, Molecular Probes, Oregon, USA) and by means of flow cytometric analyses to asses the viability of the sperm (Garner et al., 1994; Garner et al., 1995; Donoghue et al., 1995; Garner et al., 1996a; Garner et al., 1996b; Garner et al., 1997a; Garner et al., 1997b Garner et al., 1997c; Maxwell et al., 1997; Maxwell and Johnson, 1997; Penfold et al., 1997; Songsasen et al., 1997; Thomas et al., 1997; Vetter et al., 1998; Thomas et al., 1998; Chalah and Brillard, 1998).

However, it is a disadvantage of this method that the SYBR-14 is slightly toxic to spermatozoa whereby the amount of live spermatozoa in a sample will decrease over even a short time. Since a staining time of 10 to 15 minutes has been used routinely in combination with 100 nM of SYBR-14, results are likely to be inaccurate due to the decrease in live spermatozoa over time (Christensen and Stenvang, unpublished data). It is a further disadvantage of the method that the incubation of samples for staining is made at 36–37° C., which is highly inconvenient in routine work in laboratories or artificial insemination stations assessing semen quality.

In U.S. Pat. No. 4,559,309 a process for characterization of sperm motility and viability is disclosed. A sperm sample is stained with Rhodamine 123 and ethidium bromide and the fluorescence emissions of the sperm are measured by means of a flow cytometer. By measuring fluorescence emissions at green and at red wavelengths a measure correlated with sperm motility (green counts) and dead or putative dead sperm cells (red counts), respectively, is obtained. Staining of a second sample with acridine orange provides a measure of the percentage of single and double stranded DNA in the sperm cells thereby indicating mature and immature sperm and somatic cells. This process does not provide an absolute measure of the semen concentration. Furthermore, two different staining procedures are necessary to obtain a measure of sperm motility and dead or dying sperm ells and a measure of the types of sperm cells in the sample.

Furthermore, staining of mitochondria with Rhodamine 123 and DNA with PI implies that two different cellular compartments are targeted. 'Detached heads' are observed commonly in semen from normal bulls (affecting 5.3±0.4% of the sperm; Barth & Oko, 1989) and the incidence of this defect can be much higher for individual bulls. With this condition, the connected midpiece and tail will be motile and stain with R123. The detached head will stain with PI and consequently the percentage of viable or dying sperm cells in the sperm population will be estimated inaccurately.

It is further known in the art to control the sample injection to electronic counters or flow cytometers so as to obtain a measure of the concentration. However, in these methods the control of the sample injections is affected by differences between instruments, and calibration is needed at regular intervals. One example of such an instrument is Partec Sperm Cell Counter™ (Partec GmbH, Munster, Germany) where performance is unacceptable for assessment of sperm concentration in bovine semen (Dumont et al., 1996).

Further, it is known to use a standardised bead solution for absolute counting of the sperm concentration; the performance of this method was, however, found unacceptable for assessment of sperm concentration (Dumont et al., 1996).

It is common to all of the above-mentioned methods that only the ratio of live sperm cells or the concentration of the dead or killed sperm cells is determined. To obtain a determination of the ratio of live sperm cells and a determination of the concentration of the semen an evaluation of the semen sample using at least two different methods is needed.

Furthermore, a long-standing goal of the cattle artificial insemination (AI) industry is to obtain a simple, precise and accurate method for examination of bull semen that correlates highly with fertility after AI. Routine assessment of semen volume, sperm concentration, motility and wave motion in an AI stud are valuable in order to discard semen of poor quality, but appear of little value to predict the fertility of individual males (Christensen et al. 1999). In recent years, computer aided sperm analysis (CASA; Budworth et al. 1988) have provided an objective assessment of sperm motility. Disadvantages of this technique such as poor precision, bias due to program settings and sperm migration during analysis (Christensen and Stryhn, 1997) limits the potential use.

SUMMARY OF THE INVENTION

It is an object of the present invention to provide a method that permits a simultaneous determination of the concentration of sperm cells and the proportion of the live sperm cells in a semen sample.

It is a further object of the present invention to provide a method for a simultaneous determination of the concentration of sperm cells and the proportion of live, dying and dead sperm cells.

It is a still further object of the present invention to provide a method according to the above-mentioned method wherein the staining process can be performed fast and at room temperature.

The invention relates to a method for the determination of the total concentration of sperm cells in a semen sample and the proportion of live sperm cells therein, the method comprising subjecting the semen sample or a diluted subsample of the semen sample to selective staining of live and dead sperm cells and determining the total concentration of the sperm cells and the proportion of live sperm cells by means of a detection means responsive to the selective staining.

As will be explained in greater detail in the following, one way of determining the total concentration of the sperm cells and the proportion of live sperm cells is by use of flow cytometry where the detection means is a photo detector and where information relating to the concentration is obtained by incorporation of an internal standard in the form of fluorescent particles, but other determination methods based on selective staining have been developed during recent years and will also be adaptable to the method of the invention. One such method is a computer-assisted microscopy method where an image of stained particles in a cuvette of an exactly defined volume is detected by means of an array of photodetectors such as a CCD array and subjected to image processing, cf. WO 98/50777.

The information represented by the absolute concentration (by weight or by volume, the normally preferred basis being by volume) of sperm cells and the proportion of live sperm cells constitutes a relevant set of data, but it will be understood that this set can, of course, be expressed as the concentration of live sperm cells, or the concentration of dead sperm cells, or other parameters calculable on the basis of the combination of the concentration of sperm cells and the proportion of live sperm cells.

Irrespective of the manner in which the data set is expressed, it may be used for the routine evaluation of semen, e.g. for artificial insemination and for determination of the degree of dilution required for securing an adequate number of live sperm cells in each insemination dose.

The determination of the total concentration of sperm cells and of the proportion of live sperm cells is preferably performed using the same sample or subsample and in the same determination routine, that is, the sequence of determination steps performed on one and the same sample. The determination of the total concentration of sperm cells and of the proportion of live sperm cells is preferably performed substantially simultaneously and preferably in the same determination operation, that is, in the same step.

As semen samples are relatively viscous, it is normally preferred that the semen sample is diluted to form a diluted subsample. The dilution of the sample is preferably performed using a diluent which sustains viability of the sperm cells during the determination, such as phosphate-buffered saline.

The selective staining suitably comprises a staining which stains all sperm cells combined with a staining which selectively stains dead cells. The selective staining may suitably be performed using one or more fluorochromes resulting in fluorescent qualities being conferred to live sperm cells and dead sperm cells, the fluorescent quality or qualities of live cells being distinguishable, by the detection means, from the fluorescent quality or qualities of dead sperm cells, the determination being performed by selective counting of cells of each fluorescent quality. In this context, the term "selective counting" is intended to encompass any counting or calculation or image-processing method which is based on the detection performed and which will result in data indicating on the one hand the total concentration of sperm cells and on the other hand the proportion of dead cells; the latter proportion can then being easily be recalculated into the proportion of live cells, confer above.

The fluorochromes staining the sperm cells may be any fluorochromes binding to DNA. The fluorochromes normally comprise a fluorochrome capable of selectively staining dead or dying sperm cells, this fluorochrome being capable of entering a sperm cell through a leaking or defect plasma membrane, but substantially incapable of entering a sperm cell having an intact plasma membrane, and another fluorochrome capable of staining all sperm cells, this fluorochrome being capable of entering a cell through an intact cell membrane.

By suitable adaptation of the staining, it has also been found possible to selectively determine the proportion of dying sperm cell. This is typically obtained by using a lower concentration than conventionally of the fluorochrome staining all sperm cells, such as will be explained in greater detail in the following. It is thus possible to discriminate between live sperm cells and dying sperm cells. While conventional motility determinations performed by microscopy do not permit such a distinction, it is, in the method of the invention, possible to use a staining which will permit a determination of a transition phase during which the plasma membrane of the sperm cells become increasingly permeable as an indication of the sperm cells being subject to deterioration. Such sperm cells will appear motile in microscopic motility observations, but will have a much shorter active motile period than sperm cells having an intact plasma membrane (Christensen et al., unpublished data).

Dying sperm cells have a leaking or non-intact plasma membrane whereby these sperm cells are stained by the fluorochromes staining all sperm cells and also by the fluorochromes staining the dead sperm cells. The staining of the dead sperm cells will, however, be much stronger than the staining of the dying cell, whereby the intensity of the staining provides information about the state of the cell. By keeping a suitably low concentration of the fluorochrome staining all sperm cells, it becomes possible to selectively count the proportion of sperm cells which have a flurorescent quality (respective intensities of characteristic wavelengths of the two fluorochromes) distinguishable from both the live cells and the dead cells.

The sperm cells having a leaking plasma membrane will usually die shortly after this process has started. The number of dying sperm cells is usually highest when a semen sample has been frozen or has been stored for a period prior to evaluation. Therefore, this method may also be used for development and evaluation of new media for freezing or liquid storage of sperm and/or for improvement of storage and/or freezing/thawing procedures or even for development of new such procedures.

The excitation of the fluorochromes may be performed by means of light in the wavelength range about 488 nm ("blue laser"), in which case the fluorochrome staining the live sperm cells may suitably be SYBR-14, and the fluorochrome staining the dead or dying sperm cells may suitably be propidium iodide, PI.

Alternatively, the excitation of the fluorochromes may be performed by means of light in the wavelength range about 543 nm ("green laser"), in which case the fluorochrome staining the live sperm cells may suitably be MPR71292, and the fluorochrome staining the dead or dying sperm cells may be ethidium-homodimer-2, EHD2.

SYBR-14 used in standard concentrations is slightly toxic to spermatozoa whereby the amount of live spermatozoa in a sample will decrease over even a short time. Since a staining time of 10 to 15 minutes has been used in the conventional use of SYBR-14, results are likely to be slightly inaccurate due to the decrease in live spermatozoa over time (Christensen and Stenvang, unpublished data). Therefore, according to a preferred embodiment of the invention, a short staining period (2½–5 min) is used whereby toxicity of the dyes, such as SYBR-14, is reduced, facilitating the determination of sperm viability with high precision and accuracy. Furthermore, it is preferred to perform the staining of the sperm cells at a temperature below 35° C., such as at the most 30° C., e.g., at a temperature between 15° C. and 25° C., preferably at room temperature, such as about 20° C.

The fluorochrome staining all sperm cells may be used in concentrations below standard concentrations conventionally applied for such fluorochromes to avoid toxicity of dyes, such as in concentrations in the range from 25 to 75 nanomolar, preferably such as in concentrations about 50 nanomolar.

Using such concentrations below standard concentrations for staining of the live sperm cells has a number of advantages in the method of the invention; examples are given below for the combination of the fluorochromes SYBR-14 and PI, but the advantages will also be obtainable with other relevant combinations.

Firstly, as mentioned above, the use of standard concentrations of SYBR-14 for dyeing of sperm cells has proven toxic to the sperm cells. Studies have proven that a SYBR-14 concentration of 100 nM results in a decrease in the amount of live sperm cells of 0.6% pr minute, whereas no decrease in the amount of live sperm cells are found when the applied concentration of SYBR-14 is below standard concentrations as mentioned above.

Furthermore, in order to facilitate detection of the dying sperm cells, the intensity of the fluorescent signal from SYBR-14 should be minimized. The reason for this being that dying sperm cells having a leaking membrane readily absorb SYBR-14, but only slightly absorb the PI fluorochrome, wherefore the fluorescent PI signal emitted from a dying sperm cell is relatively weak. Thus, the intensity of the fluorescent response from SYBR-14 of the dying sperm cells should be minimized so as to facilitate the simultaneous detection of the weak fluorescent response from PI present in the dying sperm cells and the strong fluorescent response from SYBR-14 also present in the dying sperm cells. When a semen sample has been frozen, as many as 30% of the sperm cells may be dying sperm cells. It is therefore of utmost importance that the dying sperm cells are discriminated from the living sperm cells in order to provide a true count of live sperm cells. If standard concentrations of SYBR-14 were used, only as little as 10% of the dying sperm cells may be revealed, whereby the number of living sperm cells would be highly overestimated.

As mentioned above, an important embodiment of the method of the invention is performed using a flow cytometer, such as a laser scanning cytometer. In this case, the determination of the concentration parameter is obtained by combining the sample or subsample with an internal concentration standard means determining the total concentration of the sperm cells and the proportion of live sperm cells simultaneously by means of a detection means responsive to the selective staining and to the internal concentration standard means.

The internal concentration standard means may be any concentration standard means that can be suitably combined with the sample or subsample and detected by the detection means to function as a reference indicative of the concentration of the sperm cells. The internal concentration standard means may suitably be constituted by standardisation particles, the standardisation particles being added in a predetermined number per weight or normally volume amount of the sample or subsample. The standardisation particles are fluorescent particles, in particular fluorescent beads, having a fluorescent quality distinguishable from the fluorescent qualities of the live sperm cells, dead sperm cells, and dying sperm cells.

The size and total sperm cell concentration of the subsample may suitably be adapted so that the number of sperm cells corresponds to between one tenth and ten times the number of standardisation particles, in particular to between one quarter and four times the number of standardisation particles, such as to between half and twice the number of standardisation particles.

The beads may be provided in a suspension comprising beads and diluent. It is an advantage of a suspension comprising both the beads and the diluent that the suspension may be manufactured by a manufacturer in a highly automated process to obtain a very accurate number of beads in the suspension. Furthermore, the suspension comprising the diluent and the beads may be manufactured in tubes, the tubes being suitable as measuring chambers in fluorescent activated cell sorters, such as flow cytometers. Thereby, inaccuracies originating from redistribution and dilution of the suspension are minimized. Still further, using tubes from the same manufacturing process with the same lot number, corresponding results may be obtainable independently of different apparatuses being used by different users. For example, CD4/3 and CD813 tubes manufactured by Becton Dickinson (EP 0 568 183) containing a predetermined number of beads in a diluent may be used. Furthermore, tubes containing only beads, such as "TruCount" tubes manufactured by Becton Dickinson and containing a predetermined number of beads, may be used.

The diluent may be a diluent which is non-toxic to sperm and which sustains viability during the staining and analysis procedures. The diluent may be a diluent decreasing the staining time. The diluent may comprise any medium capable of preventing sperm cells from sticking to the side walls of the measuring chamber or measuring tube, such as a chemical compound, such as a protein, such as BSA, or another suitable compound such as polyvinyl alcohol (PVA), etc.

In order to obtain an even higher accuracy of the measurements, automated dilution of the semen may be applied. Thereby, the operator-dependant part of the process is eliminated which makes the process highly reproducible.

The determination of the concentration of the sperm cells and the proportion of live sperm cells may be determined as a mean value of the determination of the total concentration of the sperm cells and the proportion of live sperm cells performed on two or more subsamples of the semen sample. Hereby, the concentration of the sperm cells and the proportion of live sperm cells may be determined more accurate.

After the analysis of the subsample, the sample may be diluted to a predetermined semen concentration or a predetermined number of live sperm cells and distributed so as to fill one insemination dose with an appropriate number of live sperm cells for artificial insemination. An indication of the quality of the semen based on the semen concentration and the number of live sperm cells in the corresponding ejaculate may accompany the insemination dose. Thereby, the users, such as the artificial insemination stations, may obtain valuable information regarding the semen.

Furthermore, the method of the invention makes it possible to obtain a sound basis for accepting or rejecting semen from ejaculates according to whether they fulfil or do not fulfil specified values for total sperm cell concentration and proportion of live sperm cells, so as to ensure that only semen of a certain quality is used for artificial insemination.

The method of the invention may also be used to determine the absolute number of sperm cells produced by animals subjected to toxicology or other pharmacological experiments. Furthermore, the method of the invention may be used to prove that animals or human beings have been influenced by e.g. a toxicological environment or chemical invasions into the body.

Furthermore, because of the objectiveness and reproducibility of the method, the method may be used to evaluate the semen quality and quantity of human semen, both in connection with artificial insemination and in vitro fertilization and in connection with investigations of the proposed decline in human semen quality.

Another aspect of the invention relates to a method for predicting the likelihood of fertilizing a female animal by artificial insemination with an insemination dose, comprising determining the total concentration of sperm cells in the semen sample from which the insemination dose is taken or is to be taken, and the proportion of live sperm cells therein by a method as described herein, and including the thus determined total concentration of the sperm cells in the semen sample and the proportion of live sperm cells therein, or the concentration, calculable therefrom, of live sperm cells in the sample, in the parameters on the basis of which the likelihood of fertilizing the animal is predicted. The likelihood of fertilizing the female animal may be predicted on the basis of the determined total concentration of the sperm cells in the semen sample and the proportion of live sperm cells therein, or the concentration, calculable therefrom, of live sperm cells in the sample.

The prediction of the likelihood of fertilizing the female animal may be performed on the basis of statistically significant correlations between fertility data obtained in insemination experiments with several female animals and data indicating the total concentration of the sperm cells in the semen sample used in the insemination experiments and the proportion of live sperm cells therein, and/or data indicating the concentration of live sperm cells therein. The protocol for an example of suitable experiments is given in Experiment 3 below.

When the female animal is a multiparous animal, the number of offspring resulting from the fertilization may also be predicted, using data established by the method of the invention as described herein, correlated with results of suitably designed experiments.

The prediction may be performed on the basis of results obtained from a fresh ejaculate or on the basis of results obtained from a semen sample which is a frozen insemination dose, the sample being thawed before being subjected to the determination method, or on the basis of a combination of a determination on the frozen-thawed sample and a determination on the fresh ejaculate from which the frozen-thawed sample was derived. Another type of sample is a diluted and stored sample.

Another aspect of the invention is constituted by a method for artificial insemination of a female animal, comprising using, for the insemination, an insemination dose having a predicted likelihood of fertilizing the animal, as predicted by the above-described method, above a predetermined discrimination likelihood. When the female animal is a multiparous animal, and the insemination dose may be an insemination dose having a predicted likelihood of resulting in a number of offspring above a predetermined discrimination number.

DESCRIPTION OF PREFERRED EMBODIMENTS

EXPERIMENT 1

SUMMARY

Figure 1:
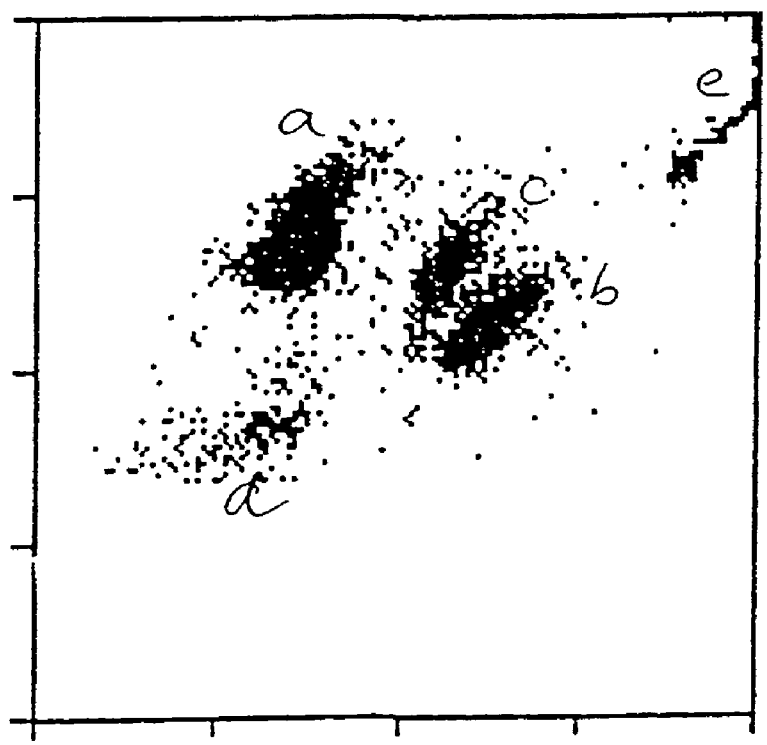
FIG. 1 shows a plot of the results from the FACSCount with 488 nm laser showing green versus red fluorescence intensity using the method of the invention. Live sperm (a), dead sperm (b) as well as dying sperm (c) can be identified and are clearly separated from debris (d) and beads (e). In this particular sample, the dying sperm accounted for 9.4% of the total sperm count.

In a first experiment, sperm concentration and viability in bull ejaculates have been determined by selective staining of the live and dead sperm cells in a semen sample and subsequently, analysing the semen samples with flow cytometry according to a preferred embodiment of the invention. For comparison purposes, the sperm concentration has also been determined using prior art methods, i.e. by determination of sperm concentration with a spectrophotometer (L'Aiglon, IMV, Cedex, France) and a particle counter (Sysmex F-820, SYSMEX, Almind, Denmark), and further using manual counting using a Makler chamber (Sefi Medical, Haifa, Israel) and a phase contrast microscope.

The analyses using flow cytometry for simultaneous determination of sperm concentration and viability in bull ejaculates at AI station were carried out using two different FACSCount flow cytometers (BDIS Europe, Erembodegem-Aalst, Belgium) equipped with a blue (488 nm), and a green (543 nm) laser, respectively. Sperm was either stained with a combination of SYBR-14 and PI for analysis with the blue (488 nm) excitation wavelength or stained with a combination of MPR71292 and EHD2 for analysis with the green (543 nm) excitation wavelength. The data obtained from the flow cytometers was subsequently analysed with Attractor™ software (BDIS Europe, Erembodegem-Aalst, Belgium). In addition to the determination of sperm concentration, the flow cytometric analyses also provided an estimate of sperm viability.

In general, a good agreement was found between the above-mentioned methods. The short staining period (2½–5 min) in combination with minimal concentration of SYBR-14, reduced the toxicity of this dye, thus, facilitating determination of sperm viability with high precision and accuracy. Furthermore, the used protocol allowed for the detection of live, dead as well as dying sperm.

Materials and Methods

Semen Samples:

The semen samples to be used in the experiments were collected from 25 bulls giving a total of 52 ejaculates. The semen samples were collected during 4 days from bulls with differences in both semen concentration and quality. An aliquot of 2–3 ml of the raw semen was placed in a tube (NUNC Intermed Cat# 347880, Lifetechnologies, Roskilde, Denmark) and placed on a Swelab-820 mixer (Bie & Berntsen, Rødovre, Denmark) and mixed continuously. All processing and analyses were carried out within 30 minutes after semen collection.

Determination of Sperm Concentration Using Makler Chamber:

Two samples of the raw semen were diluted 1:40 with a Hamilton Microlab A503 autodiluter (Struers KEBO lab., Albertslund, Denmark) and using a phosphate buffered saline (PBS, pH 7.4, 300 mOsm with 0.1% BSA). The diluted samples were placed on a mixer (Adams Nutator, NC. Nielsen, Brøndby, Denmark). Prior to evaluation, spermatozoa were immobilized by adding 7.5 µl 4% (w/v) formaldehyde and the Makler chamber was loaded with a 7.5 µl subsample. The lid of the Makler chamber was placed in position and touched gently with the tip of a fingernail to ensure that it rested firmly on the pillars (Newton rings). A total of 25 squares was counted under phase contrast microscopy using 200× magnification. After counting, the chamber was washed in distilled water, dried and reloaded with a subsample from the same sample. Subsequently, this procedure was applied for the second subsample and a total of 4 measurements (2 samples×2 replicates) was obtained per ejaculate.

Determination of Sperm Concentration Using Spectrophotometer:

A 20 µl sample of the raw semen was diluted to a total volume of 4 ml (1:200) in a cuvette for the L'Aiglon spectrophotometer. Dilution was done with a CAVRO autodiluter (Z 069, IMV). Following dilution, a small piece of foil was placed over the cuvette and the diluted sample was mixed gently by hand. After resting approximately 10 sec., the cuvette was placed in the spectrophotometer and the sperm concentration was measured. The cuvette was again covered with foil and mixed gently by hand, and after a resting period the cuvette was once more measured in the spectrophotometer. Following this measurement, a second sample was diluted and measured. Thus, a total of 4 measurements was obtained per ejaculate.

Determination of Sperm Concentration Using Particle Counter:

A two-step dilution is necessary in order to count sperm concentration on the Sysmex F-820 particle counter. The first step was dilution of 20 µl raw semen to a volume of 10 ml (1:500) and in the second step, 100 µl of the diluted semen was diluted to a total volume of 10 ml and placed in a sample-cup (1:100, resulting in a combined dilution of 1:50,000). Both dilution steps were performed with an AD-270 autodiluter (SYSMEX, Almind, Denmark). The sample-cup was covered with a small piece of foil and mixed gently by hand and rested for approximately 10 sec. before counting on the Sysmex. After counting, the sample-cup was again covered with foil, mixed and counted once more. The sample was then discarded and a second sample was diluted, treated and counted according to this procedure. A total of 4 counts was obtained per ejaculate.

Determination of Sperm Concentration and Viability Using Flow Cytometer:

A two-step dilution is necessary for the flow cytometric analyses. First, the sample is diluted 250× in a PBS medium containing 0.1% BSA, (NUNC Intermed Cat# 3478880, Lifetechnologies, Roskilde, Denmark), and second a 20 µl sample is transferred to a Sperm Count tube containing approximately 100,000 beads using reverse manual pipetting. The dyes were added to the Sperm Count tubes less than 12 hours before using the tubes in the analysing procedure. As mentioned above, two different flow cytometers were used, one being a FACSCount equipped with a green (543 nm) laser and the second being a FACSCount equipped with a blue (488 nm) laser.

To each Sperm Count tube to be analysed in the first FACSCount (543 nm), 2 µl of MPR71292 and 2 µl of EHD-2 were added to provide final concentrations of 100 nM and 5 µM, respectively.

To each Sperm Count tube to be analysed in the second FACSCount (488 nm), 5 µl of SYBR-14 and 5 µl of PI were added to provide for final concentrations of 50 nM and 12 µM, respectively.

Prior to opening the Sperm Count tubes, the tubes were whirlmixed for 3 sec in an upside-down position and for 3 sec in a normal position. Whirlmixing were repeated for two sec after addition of the sperm and before each analysis. After addition of sperm, the Sperm Count tubes were placed on a mixer (Adams Nutator, N. C. Nielsen, Brøndby, Denmark) for 4 min at room temperature with no light reaching the tube. After 4 min, the first replicates were analysed simultaneously on the two flow cytometers and the second replicates were analysed after a 6 min staining period. Tubes were analysed twice to provide for a second replicate rather than pipetting two subsamples from the tubes. A total of 4 analysis was carried out on each flow cytometer per ejaculate.

Analysis of FACSCount Data:

During the flow cytometric analyses, data were stored on a floppy disk in the FACSCount, and after the measurements, data from the floppy disk were analysed using Attractor™ (BD) software at the Royal Veterinary and Agricultural University, Section for Reproduction.

Statistical Analysis:

Data obtained from the five methods (Makler chamber, spectrophotometer (L'Aiglon), particle counter (Sysmex), and flow cytometers (FACSCount with green or blue laser) were subject to analyses of variance to point out significant effects of date, bull, sample, replicate, combinations of these effects as well as residual variation. Viability data from the FACSCount analyses were also subject to analyses of variance. The following statistical model (1) was used:

(1) $Y_i = \alpha_{i,date} + B_{i,bull} + C_{i,bull*date} + D_{i,date*bull*sample} + \epsilon_i$ where:
$Y_1$ = result for the method
$\alpha_{i,date}$ = effect of date (systematic)
$B_{i,bull}$ = effect of bull
$C_{i,bull*date}$ = effect of ejaculate
$D_{i,date*bull*sample}$ = effect of sample
$\epsilon_i$ = residual error
i = the number of observation (measurement), 1, . . . 208

Capital letters in the above model indicate random effects. However, estimates for overall sample and replicate differences were made in a statistical model with systematic effect of sample, replicate and date.

Data from the four methods (spectrophotometer, particle counter, flow cytometer with green or blue laser) were subject to regression analyses to compare the results of these methods with results obtained with the Makler chamber. Regression analyses were based on average values for the four measurements per ejaculate for each of the methods. At first, regression analyses were made without corrections, but due to the large variation of the Makler chamber data, regression analyses were also made using a measurement error model which takes the imprecision of the Makler chamber into account. All statistical analyses were performed with SAS version 6.12 (SAS, 1990).

As can be seen from FIGS. 3–6 showing the regression lines for the results from each of the four methods against the manual counting from the Makler chamber, the concentration of the sperm cells vary from $200*10^6$ to $3000*10^6$. This variation is a variation between bulls as well as a variation between ejaculates from each bull as also indicated in the statistical method above.

Makler Chamber:

The data obtained with the Makler chamber appeared more imprecise than anticipated from earlier studies and the coefficient of variation was 21.3%.

Precision of the Spectrophotometer Method:

The results of the analyses of variance for data obtained with the spectrophotometer are shown in table 1. The instrumental coefficient of variation (CV %) is 2.10% and the large variation between samples within ejaculates (sample variation) make the method significantly more imprecise, and the 95% confidence interval for determination of sperm concentration with the L'Aiglon spectrophotometer is $\pm 169 \times 10^6$ sperm/ml when a single measurement is made (one sample, one measurement). A small overall variation in concentration was detected between the two samples with sample 1 being $48.5 \pm 15 \times 10^6$ sperm/ml lower than sample 2. The reason for this difference is unclear.

Figure 2A:
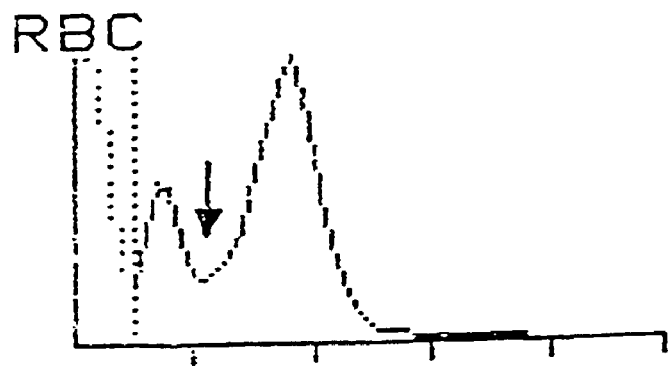
FIGS. 2A and 2B show results from the assessment of sperm concentration on the Sysmex particle counter. A difference between the first discrimination (arrows) and the second discrimination (dotted vertical line) led to differences in sperm concentration of $750 \times 10^6$ sperm/ml and $700 \times 10^6$ sperm/ml, respectively. Note that the Sysmex is designed for hematology counting and that the sperm is counted in the canal for red blood cells (RBC). The x-axis indicate the size of the particle according to the Coulter principle and the curve illustrates the distribution of particles in relation to size.
Figure 2B:
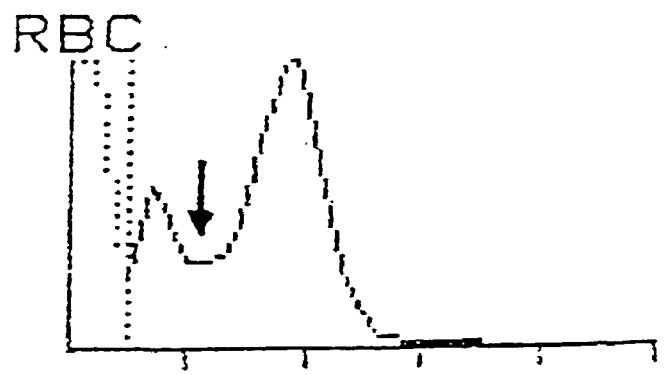
Figure 3:
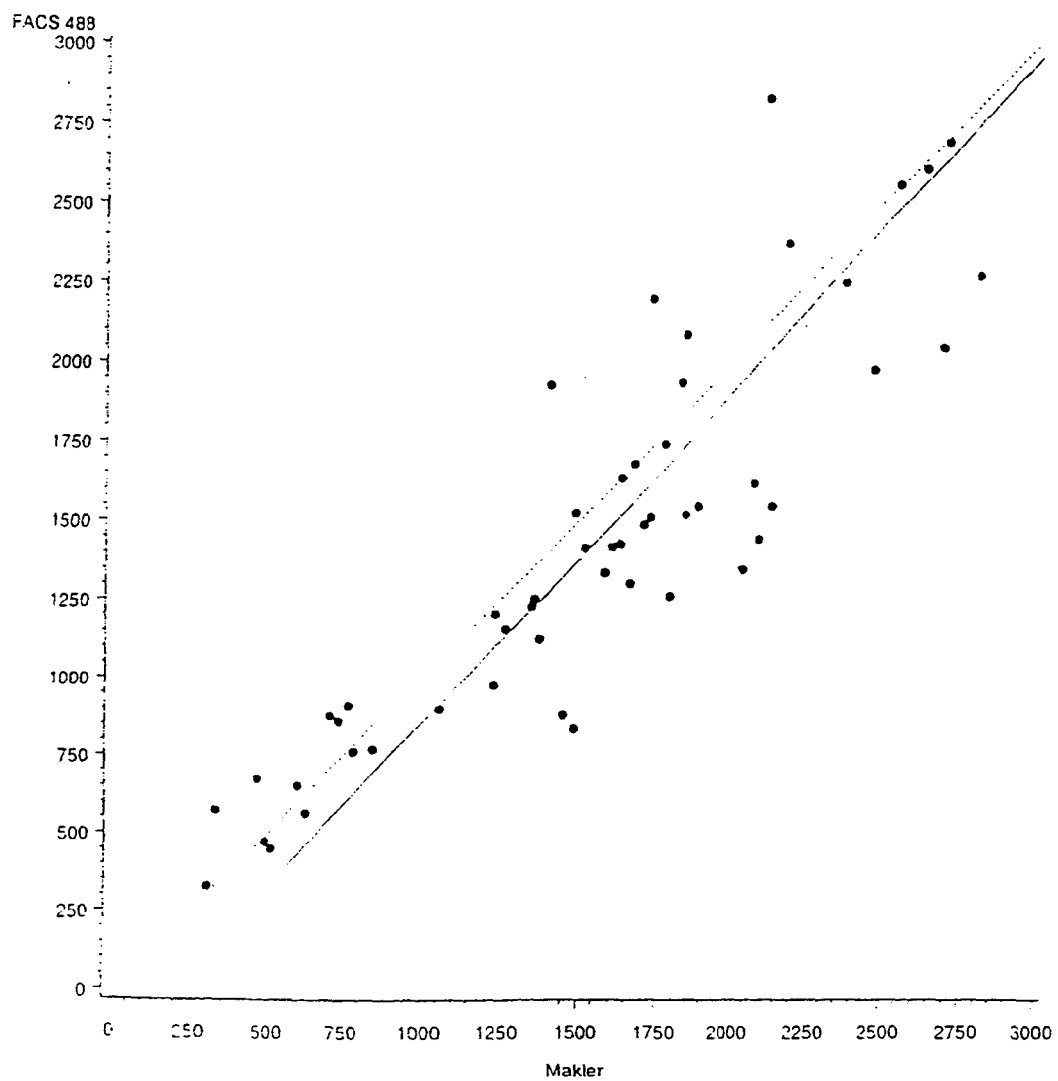
FIG. 3 shows the regression line for FACSCount with blue laser (488 nm) against Makler Chamber. The data are corrected data from the measurement error model.
Figure 4:
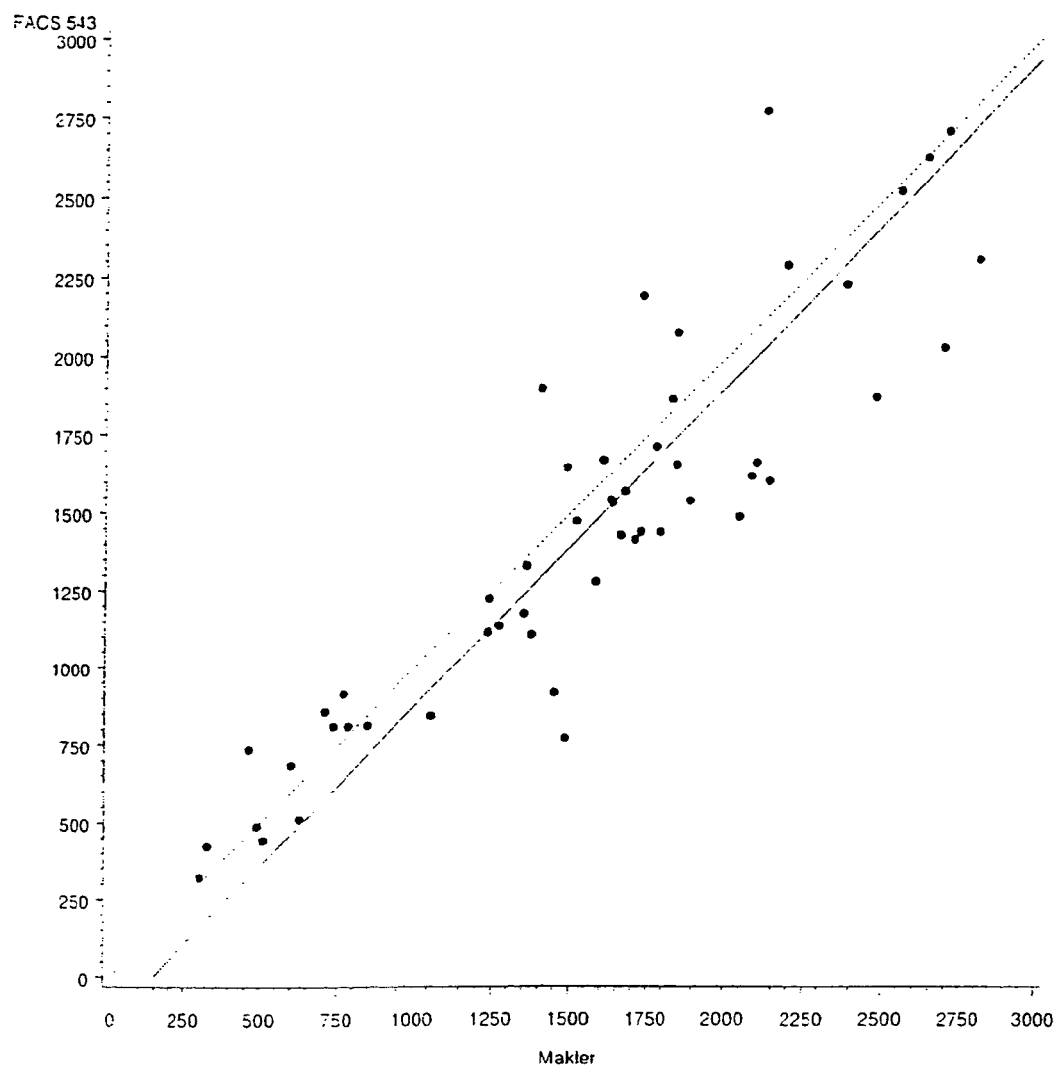
FIG. 4 shows the regression line for FACSCount with green laser (543 nm) against Makler Chamber. The data are corrected data from the measurement error model.
Figure 5:
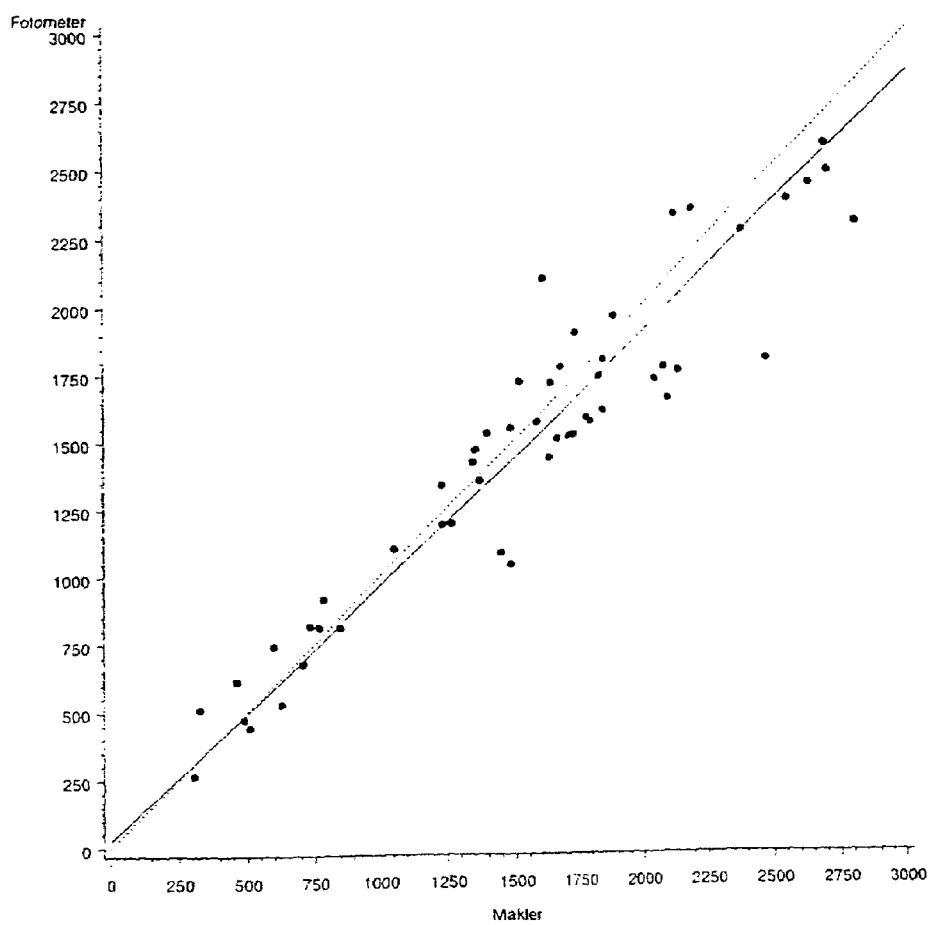
FIG. 5 shows the regression line for Spectrophotometer (L'Aiglon) against Makler Chamber. The data are corrected data from the measurement error model.
Figure 6:
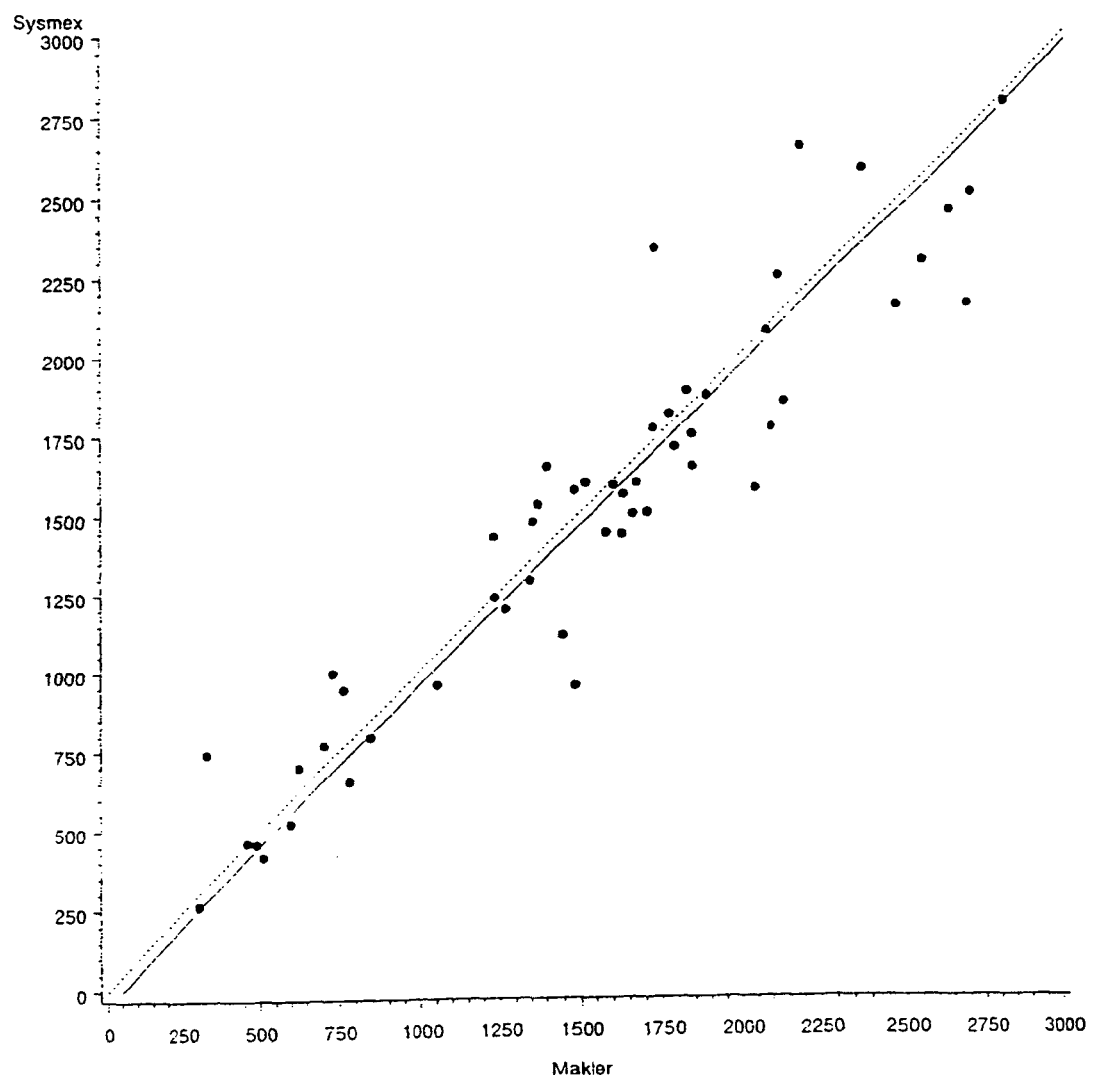
FIG. 6 shows the regression line for particle counter (Sysmex) against Makler Chamber. The data are corrected data from the measurement error model.

Precision of the Particle Counter Method:

Table 1 also shows the results for the Sysmex particle counter. The coefficient of variation with this method is high, 6.1%. In the measurements two sets of counts were used where the discrimination on particle size differed in the two replicates, respectively, in- and excluding a population of smaller particles in the "sperm count" (see FIGS. 2A and 2B). If these observations are excluded, the coefficient of variation for the Sysmex is 4.0%. The sample variation with the Sysmex particle counter is small and the 95% confidence interval of the method for a single measurement per ejaculate is $\pm 118 \times 10^6$ sperm/ml (two sets of counts mentioned above are excluded in this calculation, if included the 95% confidence interval is $\pm 182 \times 10^6$ sperm/ml).

TABLE 1

Sources of variation for the four methods: spectrophotometer (L'Aiglon), particle counter (Sysmex) and FACSCount (green laser) and FACSCount (blue laser). Numbers in brackets indicate the percentage of the total variation for the methods.

| Source of variation | L'Aiglon | | Sysmex | | FACSCount (green laser) | | FACSCount (blue laser) | |
|---|---|---|---|---|---|---|---|---|
| Bull[1] | 179,312 | (52) | 197,497 | (51) | 220,714 | (58) | 226,901 | (59) |
| Bull*date[2] | 155,884 | (45) | 186,918 | (48) | 153,674 | (40) | 151.766 | (39) |
| Bull*date*sample[3] | 6.462 | (1.9) | 64 | (~0) | 4,896 | (1.3) | 1,554 | (0.4) |
| Residual[4] | 968 | (0.3) | 3,599 | (0.9) | 3,755 | (1.0) | 7.285 | (1.4) |
| CV %[5] | 2.10 | | 4.0* | | 4.3 | | 6.0 | |
| 95% confidence int.[6] | ±169 × $10^6$ | | ±118 × $10^{6**}$ | | ±182 × $10^6$ | | ±84 × $10^6$ | |

[1]Overall variation between bulls
[2]Variation between ejaculates within bulls. (ejaculate variation)
[3]Variation between samples (sample variation)
[4]Residual variation (instrumental variation)
[5]Instrumental coefficient of variation
[6]95% confidence interval for a single measurement per ejaculate (one sample, one replicate)
*6.1% if all measurements are included
**±182 × $10^6$ sperm/ml if all measurements are included Precision of the Particle Counter Method:

Table 1 also shows the results for the Sysmex particle counter. The coefficient of variation with this method is high, 6.1%. In the measurements two sets of counts were used where the discrimination on particle size differed in the two replicates, respectively, in- and excluding a population of smaller particles in the "sperm count" (see FIGS. 1 and 2). If these observations are excluded, the coefficient of variation for the Sysmex is 4.0%. The sample variation with the Sysmex particle counter is small and the 95% confidence interval of the method for a single measurement per ejaculate is ±118×$10^6$ sperm/ml (two sets of counts mentioned above are excluded in this calculation, if included the 95% confidence interval is ±182×$10^6$ sperm/ml).

Precision of the Facscount with Green Laser (543 nm):

The results of the FACSCount with green laser is shown in table 1. The coefficient of variation is 4.3% and the 95% confidence interval for a single measurement per ejaculate is ±182×$10^6$ sperm/ml. It should be noted that no significant differences are observed between replicates or samples.

Precision of the FACSCount with Blue Laser (488 nm):

The results of the FACSCount with blue laser (table 1) have a higher coefficient of variation (6.0%) but due to less variation between samples the 95% confidence interval for a single measurement per ejaculate is ±184×$10^6$ sperm/ml. A higher sperm concentration was observed for replicate 2 (54.7±11×$10^6$ sperm/ml higher than replicate 1). The reason for this difference was unclear.

Precision of the FACSCount (Green Laser) for Determination of Sperm Viability:

The results for determination of sperm viability with FACSCount (green laser) are shown in table 2. Coefficient of variation for the method is 1.2%. The 95% confidence interval for determination of sperm viability based on one measurement per ejaculate is ±4.0%. A small decrease in sperm viability over time was observed (−0.27±0.07%/min). This decrease is much less than decreases observed in trials using a staining time of more than 10 minutes. With a staining time of 3–5 minutes, the accuracy of the method is only affected slightly.

Precision of the FACSCount (Blue Laser) for Determination of Sperm Viability:

The results of the FACSCount (blue laser) for determination of sperm viability are shown in table 2. The coefficient of variation is equal (CV=1.1%) to that of the FACSCount with green laser but due to a slightly larger sample variation, the 95% confidence interval for a single measurement per ejaculate is 6.2%. Sperm viability did not decrease over time (−0.15±0.07%/min) which are a likely effect of the reduced concentration of the SYBR-14 stain (50 nM)).

TABLE 2

Sources of variation for flow cytometric determination of sperm viability. Numbers in brackets indicate the percentage of the total variation of the method.

| | FACSCount (green laser) | | FACSCount (blue laser) | |
|---|---|---|---|---|
| Bull[1] | 29.73 | (65.8) | 24.16 | (45.8) |
| Bull*date[2] | 11.24 | (24.9) | 18.75 | (35.5) |
| Bull*date*sample[3] | 3.26 | (7.2) | 9.01 | (17.0) |
| Residual[4] | 0.94 | (2.1) | 0.83 | (1.6) |
| CV %[5] | 1.2 | | 1.1 | |
| 95% confidence int.[6] | ±4.0% | | ±6.2% | |

[1]Overall variation between bulls
[2]Variation between ejaculates within bulls. (ejaculate variation)
[3]Variation between samples within ejaculates (sample variation)
[4]Residual variation (instrumental variation)
[5]Instrumental coefficient of variation
[6]95% confidence interval for a single measurement per ejaculate (one sample, one replicate)

Regression Analyses

The regression lines for the four methods after correction for imprecision of the "golden standard" are shown in FIGS. 3 to 6 and the results of the regression analyses are shown in table 3. The concentrations of sperm cells in the semen samples vary from 200*$10^6$ to 3000*$10^6$ sperm cells pr. ml. The slopes of all regression lines are not significantly different from 1 and the intercepts for the different regression lines are not significantly different from 0. It appears from table 3, that the error of the FACSCount analyses are higher than for the spectrophotometer and particle counter. Correlation coefficients from the regression analyses without correction showed a slightly lower correlation for the analyses with FACSCount where the correlation for respectively the green and blue laser were 0.91 and 0.9 versus 0.945 for particle counter and 0.96 for spectrophotometer. This is in contrast to results obtained earlier where the correlation coefficients for respectively particle counter, spectrophotometer and FACSCount were 0.93, 0.93 and 0.97. In theory, the correlation for the FACSCount (either laser) should be higher than those of the other methods because the flow cytometric method identifies sperm from a staining of DNA. However, since bull semen contains a very little amount of debris, the difference between the results obtained using flow cytometry and the results obtained using other techniques is small.

General Discussion

Sperm viability: The two methods for determination of sperm viability are highly accurate and only for the combination of 292 and EHD2 a slight decrease in viability (−0.27±0.07%/min) was observed. Since analyses can be performed after a 2½ min staining time, viability can be determined precisely as well as accurately. It may be desirable to stain two samples per ejaculate since sample difference is a significant source of variation. With two samples per ejaculate, the 95% confidence interval for the determination of sperm viability will be from 2.8% (green laser) to 4.4% (blue laser). Using the described techniques, sperm viability can be determined with a far higher degree of precision and accuracy than possible with microscopic evaluation of sperm motility. This implies that the fertility of a semen sample can be predicted more accurately from sperm viability data. The correlation between sperm viablity and fertility is demonstrated in experiment 3

TABLE 3

Results of the regression analyses (corrected for imprecision of the Makler chamber). Values ± standard deviation (sd).

| Method | intercept (α) | slope (β) | error |
|---|---|---|---|
| FACSCount (green laser) | −150 ± 115 | 1.03 ± 0.07 | 70 |
| FACSCount (blue laser) | −200 ± 130 | 1.05 ± 0.08 | 70 |
| Spectrophotometer (L'Aiglon) | 20 ± 75 | 0.94 ± 0.05 | 40 |
| Particle Counter (Sysmex) | −50 ± 85 | 1.01 ± 0.05 | 40 |

Figure 7:
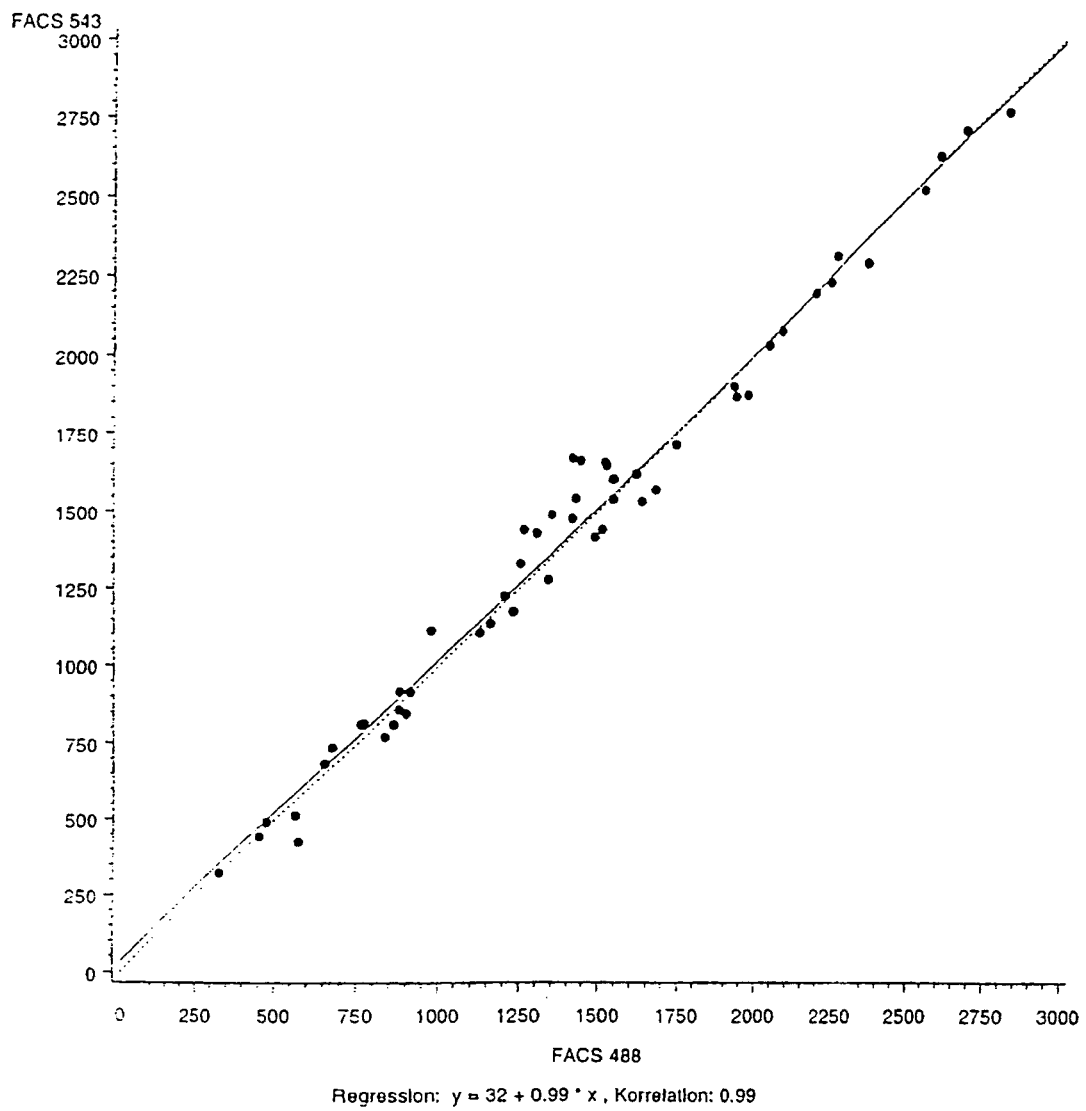
FIG. 7 shows the regression line for FACSCount with green laser (543 nm) against FACSCount with blue laser (488 nm). The uncorrected data show a very high correlation between these techniques. The slope $\beta$ is 0.99 and the correlation coefficient is 0.99.

Sperm concentration: Determination of sperm concentration with FACSCount (either laser) is in the present investigation very close to the results achieved using the particle counter (Sysmex) or the spectrophotometer (L'Aiglon) and the correlation between FACSCount methods are very high (FIG. 7). In both flow cytometric methods 5000 events were sampled per analysis, and it is believed that still better results may be obtained by a sampling of 10000 events.

A significant source of variation for the flow cytometric determination of sperm concentration is the difference between samples. This difference relates both to true difference between samples and to difference between Sperm Count tubes. The variation between samples may be reduced by applying a fully automated dilution procedure thereby reducing the operator dependent factor to a minimum. Furthermore, the results of the method may be improved by a determination of the sperm concentration for an ejaculate based on a mean value obtained from analyses of two Sperm Count tubes. Thereby, also the influence of variation in bead number between individual Sperm Count tubes could be reduced, and furthermore the sperm viability would be determined more precisely if it was based on two samples.

EXPERIMENT 2

SUMMARY

In a second experiment, sperm concentration and viability in boar ejaculates have been determined according to a preferred embodiment of the present invention. Live and dead sperm cells in boar semen samples have been stained selectively, and subsequently the semen samples have been analysed with FACSCount flow cytometers equipped with either a 488 nm or a 543 nm laser. A total of 58 ejaculates was analysed on each of the two flow cytometers and on a spectrophotometer (Corning 254). Furthermore, the sperm were counted in a Thoma haemacytometer using phase contrast microscopy at 200× magnification.

The results of this experiment show that determination of sperm concentration with the two flow cytometric techniques results in a higher precision and accuracy than obtained with the Corning 254 spectrophotometer. Gel-particles, present in large number in boar semen, increase the turbidity of boar semen and make spectrophotometric measurements unreliable. It is a significant advantage of the flow cytometric technique that it provides for a more precise and accurate sperm count and simultaneously provides for a precise determination of sperm viability.

Materials and Methods:

Semen Samples:

A total of 58 boar ejaculates has been analysed. Two subsamples from each ejaculate were diluted 250× in a PBS medium containing 0.1% BSA and a 60 µl aliquot was transferred to a Sperm Count tube. The staining times for SYBR-14/PI as well as for MPR71292/EHD2 were 4 mins and the tubes were subsequently analyzed on two FACSCount flow cytometers equipped with a 488 nm laser and a 543 nm laser, respectively.

The 58 ejaculates were collected from 40 boars. From each ejaculate a 3 ml aliquot was taken and placed in a tube (NUNC Intermed Cat #347880, Lifetechnologies, Roskilde, Denmark) and placed on a Swelab-820 mixer (Bie & Berntsen, Rødovre, Denmark) and mixed continuously. All the subsequent analyses were carried out within 30 mins after semen collection.

Determination of Sperm Concentration Using Thoma Haemacytometer:

Raw semen was diluted in a 5% w/v sodium-chloride solution. The dilution ratio varied according to the sperm concentration determined using the spectrophotometric method in order to achieve an appropiate number of sperm cells in the Thoma haemacytometer.

Thus, the most concentrated samples were diluted 72×, whereas the 'thin' samples only were diluted 16×. Samples were placed on a mixer (Adams Nutator, N. C. Nielsen, Brøndby, Denmark) during counting. The lid of the Thoma haemacytometer was placed in position on the two pillars (Newton rings) and the two counting areas were filled with a capillary tube. In each half of the counting chamber, 5 large fields of each 6 small squares were counted. The counting chamber was filled twice by each of the two persons involved in the counting.

Determination of Sperm Concentration Using Spectrophotometer (Corning 254):

For spectrophotometric determination of sperm concentration, 0.25 ml of raw semen was diluted with 9.75 ml EDTA solution in a cuvette. The sperm concentration was subsequently measured and the cuvette was mixed gently by hand and re-measured. A subsequent sample was treated likewise, thus, 4 measurements were made per ejaculate.

Determination of Sperm Concentration and Viability Using Flow Cytometer:

The dilution of samples for the flow cytometric analyses were performed as described for bull semen (experiment 1), apart from a volume of 60 µl of the 250× diluted sample being transferred to each Sperm Count tube using reverse manual pipetting. The dye concentrations and the protocol of analysis are identical to those mentioned above.

RESULTS AND DISCUSSION

The coefficient of variation for the flow cytometric determination of sperm concentration were 3.2% and 3.1% for FACSCount flow cytometers equipped with a 488 nm laser and a 543 nm laser, respectively. For comparison, the coefficient of variation for the spectrophotometric measurements were 5.9% indicating a larger imprecision of this technique. Furthermore, the data for the spectrophotometric measurements was more randomly distributed around the regression line than the data obtained using the flow cytometric measurements. In the measurement error model, the standard deviation was 40 for the spectrophotometric method which should be compared to a standard deviation of 20 for the results obtained using the two flow cytometers. The coefficient of variation for the determination of sperm viability was 1.4% for both flow cytometric techniques.

Determination of sperm concentration in boar semen is difficult due to a large amount of gel-particles making the spectrophotometric readings inaccurate. Likewise, the results obtained using particle counters, such as the Sysmex used for bull semen, will provide inaccurate readings due to the large amount of gel-particles with a size corresponding to the size of the spermatozoa, and furthermore, the flow system of a particle counter is often obstructed by large gel-particles also present in the boar semen. The determination of sperm concentration using flow cytometric methods is significantly more accurate and precise than spectrophotometric measurements and, furthermore, obstruction of the flow system due to large particles is a rare event. The high precision of the flow cytometric methods when used on boar semen is explained by the large amount of gel particles present in boar semen, making the prior art methods highly inaccurate. Still further, the flow cytometric method provides an objective and precise determination of sperm viability, the method being significantly more precise than conventional, subjective microscopic assessment of sperm motility.

EXPERIMENT 3

SUMMARY

An important application of the flow cytometric methods described above is the possibility to predict the fertility according to the predetermined sperm concentration and sperm viability. To assess the value of this technique for the selection of semen samples for artificial insemination (AI), a large scale fertility trial with bull semen have been performed. In the present experiment there has been used SYBR-14 in a concentration of 50 nM and PI in a concentration of 12 µM. Four ejaculates from each of 157 bulls (Holstein or Jersey breeds) have been analyzed fresh and frozen-thawed using flow cytometric methods and computer assisted sperm analysis (CASA). Furthermore, the fresh semen was subjected to morphological evaluation of the semen, and standard routine evaluation of the semen samples were carried out in the involved bull stations. A total of 121.232 inseminations with insemination doses provided from the 4×157 ejaculates were performed in Danish cattle herds. Preliminary data from this extensive trial shows that the flow cytometric determination of sperm viability explains 30 to 50% of the variation in fertility after insemination. In contrast, routine evaluation only explained approximately 10% of this variation and computerized determination of sperm motility was only slightly better than the microscopic evaluation used rutinely. In conclusion, the flow cytometric determination of sperm viability allows a more precise selection of semen samples for AI and this technique is of great value to cattle breeders worldwide.

Materials and Methods:

Semen from a total of 157 bulls were collected 4 times each with an interval of one week. Semen volume was assessed and the sperm concentration was determined using particle counter. Sperm motility and wave motion was determined using a phase contrast microscope at 200× and 100× magnification, respectively. Morphological evaluation was performed on two Eosin-Nigrosin stained smears per ejaculate. Computer analysis of sperm motility were performed with a HTM IVOS system (Christensen and Stryhn 1997). To avoid time-dependent bias, 20 fields were acquired randomly in two Makler chambers. Flow cytometric analyses were performed using modified FACSCount flow cytometers.

In total, 121.232 inseminations were performed randomly in Danish cattle herds. Fertility data and data from the semen analyses were analyzed using mixed linear models.

Results and Discussion:

Previous studies have shown a limited value of the subjective evaluation of sperm motility with regard to prediction of fertility of a semen sample. Staining of bull sperm with SYBR-14 and PI and subsequent analysis on a FACScount flow cytometer as performed according to a preferred embodiment of the present invention, provides an objective and precise determination of viability, and furthermore a precise determination of sperm concentration. As described above, this method allows for simultaneous detection of live, dead and dying sperm, and preliminary data from the first statistical analyses show a high correlation to fertility in vivo. Approximately 30 to 50% of the variation in fertility after insemination can be explained from the viability parameter. In contrast, microscopic routine evaluation of sperm motility only explains approximately 10% of the variation. Sperm viability determined using flow cytometric methods represents the first technique that makes it possible to improve fertility significantly by culling poor semen samples in the lab of a bull station. Because of the high precision of this technique, it is possible to point out ejaculates where an unacceptable result after insemination can be anticipated. Such ejaculates can therefore be discarded and the overall fertility can be improved. The same correlation appears likely for a range of different species, but the precise value of the technique can only be clarified in fertility trials for each species/breed. At present, such a trial is in progress with boar semen.

REFERENCES

Donoghue A M, Garner D L, Donoghue D J, Johnson L A, 1995: Viability Assessment of Turkey Sperm Using Fluorescent Staining and Flow Cytometry. Poultry Sci, 74:1191–1200.

Donoghue A M, Thistlethwaite D, Donoghue D J, Kirby J D, 1996: A New Method for Rapid Determination of Sperm Concentration in Turkey Semen. Poultry Sci., 75:785–789.

Dumont P, Coupet H, Gary F, 1996: Some aspects of evaluation of semen quality and processing in France. Proc. 8th European AI-Vets meeting.

Evenson D P, Parks J E, Kaproth M T, Jost L K, 1993: Rapid Determination on Sperm Cell Concentration in Bovine Semen by Flow Cytometry. J Dairy Sci 76:86–94.

Fenton S E, Ax R L, Cowan C M, Coyle T, Gilbert G R, Lenz R W: Validation and Application of an Assay of Deocyribonucleic Acid to Estimate Concentrations of Bull Sperm. J. Dairy Sci., 73:3118–3125.

Foote RH, 1972: How to Measure Sperm Cell Concentration by Turbidity (Optical Density). Proceedings 4th Techn. Conf. on Anim. Reprod. and AI, NAAB, pp. 2–6.

Garner D L, Johnson L A, Yue S T, Roth B L, Haugland R P, 1994: Dual DNA Staining Assessment of Bovine Sperm Viability Using SYBR-14 and Propidium Iodide. J Androl, 15:620–629.

Garner D L and Johnson L A, 1995: Viability Assessment of Mammalian Sperm Using SYBR-14 and Propidium Iodide. Biol Reprod, 53:276–284.

Garner D L, Dobrinsky J R, Welch G R, Johnson L A, 1996a: Porcine Sperm Viability, Oocyte Fertilization and Embryo Development after Staining Spermatozoa with SYBR-14. Theriogenology, 45:1103–1113.

Garner D L, Johnson L A, Allen C H, Palencia D D, Chambers C S, 1996b: Comparison of Seminal Quality in Holstein Bulls as Yearlings and as Mature Sires. Theriogenology, 45:923–934.

Garner D L, Thomas C A, Joerg H W, DeJarnette J M, Marshall C E, 1997a: Fluorometric Assessments of Mitochondrial Function and Viability in Cryopreserved Bovine Spermatozoa. Biol Reprod, 57:1401–1406.

Garner D L, Thomas C A, Allen C H, 1997b: Effect of Semen Dilution on Bovine Sperm Viability as Determined by Dual-DNA Staining and Flow Cytometry. J Androl, 18:324–331.

Garner D L, Thomas C A, Allen C H, Sasser R G, 1997c: Effect of Cryopreservation on Bovine Sperm Viability as Determined by Dual DNA Staining. Reprod Domest Anim, 32:279–283.

Maxwell W M and Johnson L A, 1997: Chlortetracycline Analysis of Boar Spermatozoa After Incubation, Flow Cytometric Sorting, Cooling, or Cryoperservation. Mol Reprod Dev, 46:408–418.

Maxwell W M, Welch G R, Johnson L A, 1997: Viability and Membrane Integrity of Spermatozoa after Dilution and Flow Cytometric Sorting in the Presence or Absence of Seminal Plasma. Reprod Fertil Dev, 8:1165–78.

Parks J E, Ehrenwald E, Foote R H, 1985: Counting mammalian spermatozoa in biological fluids containing particulate matter. J. Dairy Sci., 68:2329.

Penfold L M, Garner D L, Donoghue A M, Johnson L A, 1997: Comparative Viability of Bovine Sperm Frozen on a Cryomicroscope or in Straws. Theriogenology, 47:521–530.

Songsasen N, Betteridge K J, Leibo S P, 1997: Birth of Live Mice Resulting from Oocytes Fertilized In Vitro with Cryopreserved Spermatozoa. Biol Reprod, 56:143–152.

Szollosi J, Takacs T, Balazs M, Gaspar R, Matyus L, Szabo G, Tron L, Resli I, Dajanovich S, 1986: Flow-cytometric evaluation of bull semen. 1. Objective determination of sperm cell counts in diluted semen samples. Magyar Allatorvosok Lapja, 41:459–463.

Takacs T, Szollosi J, Balazs M, Gaspar R, Matyus L, Sazabo G, Tron L, Resli I, Damjanovich S: Flow cytometric determination of the sperm cell number in diluted bull semen samples by DNA staining method. Acta. Bichim. Biophys. Hung., 22:45–57.

Takizawa S, Katoh C, Fukatsu N, Horii I, 1994: Evaluation of rat sperm viability and number by flow cytometry. Teratology, 50:40B.

Takizawa S, Katoh C, Fukatsu N, Horii I, 1995: Flow Cytometric Analysis for the Evaluation of the Rat Sperm Viability and Number in the Male Reproductive Tocicity Studies. Cong. Anom, 35:177–187.

Takizawa S, Katoh C, Inomata A, Horii I, 1998: Flow cytometric analysis for sperm viability and counts in rats treated with trimethylphosphate or pyridoxine. J. Toxicol. Sci. 23:15–23.

Thomas C A, Garner D L, DeJarnette J M, Marshall C E, 1997: Fluorometric Assessments of Acrosomal Integrity and Viability in Cryopreserved Bovine Spermatozoa. Reprod Biol, 56:991–998.

Thomas C A, Garner D L, DeJarnette J M, Marshall CE, 1998: Effect of Cryopreservation on Bovine Sperm Organelle Function and Viability As Determined by Flow Cytometry. Biol Reprod, 58:786–793.

Vetter C M, Miller J E, Crawford L M, Armstrong M J, Clair J H, Conner M W, Wise D L, Skopek T R, 1998: Comparison of motility and membrane integrity to assess rat sperm viability. Reprod Toxicol, 12:105–114.

Woelders H, 1990: Overview of in vitro methods for evaluation of semen quality. Boar Semen Preservation II, Reprod. Domest. Anim, Suppl 1:145–164.

Yamamoto T, Mori S, Yoneyama M, Imanishi M, Takeuchi M, 1996: Estimation of rat sperm with flow cytometer (FCM): simultaneous analysis of sperm number and sperm viability. Teratology, 54:38A.

Chalah T, Brillard J P, 1998: Comparison of assessment of fowl sperm viability by eosin-nigrosin and dual flourescence (SYBR-14/PI). Theriogenology, 50:487–493.

Amann RP 1989: Can the fertility potential of a seminal sample be predicted accurately? J Androl 10, 89–98.

Budworth P R, Amann R P, Chapman P L, 1988: Relationhips between computerized measurement of motion of frozen-thawed bull spermatozoa and fertility. J Androl 9, 41–54.

Christensen P, Stryhn H, 1997: Time-dependent bias in the assessment of bull semen by computer-aided sperm analysis. Biol Reprod 56, Suppl 1, 173.

Christensen P, Brockhoff P B, Lehn-Jensen H, 1999: The Relationship between Semen Quality and the Nonreturn Rate of bulls. Reprod Dom Anim 34, 503–507.

Barth A D, Oko R J, 1989: Abnormal Morphology of Bovine Spermatozoa. 1st edition, Iowa State University Press, pp 160–163.

The invention claimed is:

1. A method for the determination of the absolute concentration of sperm cells in a semen sample and the proportion of live sperm cells therein, comprising subjecting the semen sample to selective staining, wherein said selective staining comprises applying a first fluorochrome which binds to DNA and stains all sperm cells and a second fluorochrome which binds to DNA and selectively stains dead and dying cells, and determining the absolute concentration of the sperm cells and the proportion of live sperm cells by means of a detection means responsive to the selective staining, wherein the determination of the absolute concentration of sperm cells and of the proportion of live sperm cells in the semen sample are performed simultaneously in the same determination step.

2. The method according to claim 1, further comprising diluting the sample using a diluent which sustains viability of the sperm cells during the determination.

3. The method according to claim 1, wherein the selective staining is performed using one or more fluorochromes resulting in fluorescent qualities being conferred to live sperm cells and dead sperm cells, the fluorescent quality or qualities of live sperm cells being distinguishable, by the detection means, from the fluorescent quality or qualities of dead sperm cells, and the determination is performed by selective counting of cells of each fluorescent quality.

4. The method according to claim 1, further comprising determining the dying sperm cells, the selective staining being adapted to allow distinction, by the detection means, between dying sperm cells and on the one hand dead sperm cells and on the other hand live sperm cells.

5. The method according to claim 4, wherein the selective staining is performed using one or more fluorochromes resulting in fluorescent qualities being conferred to live sperm cells, dead sperm cells and dying sperm cells, the fluorescent quality or qualities of live sperm cells, dead sperm cells and dying sperm cells being distinguishable from each other by the detection means, and the determination is performed by selective counting of cells of each fluorescent quality.

6. The method according to claim 1, wherein said second fluorochrome being capable of entering a sperm cell through a leaking or defect plasma membrane, but substantially incapable of entering a sperm cell having an intact plasma membrane, and said first fluorochrome being capable of entering a cell through an intact cell membrane.

7. The method according to claim 3, wherein the excitation of the fluorochromes is performed by means of light in the wavelength range about 488 nm, the first fluorochrome staining all sperm cells being SYBR-14, and the second fluorochrome staining the dead or dying sperm cells-being propidium iodide.

8. The method according to claim 7, wherein the first fluorochrome staining all sperm cells is used in total concentrations in the range from 25 to 75 nanomolar.

9. The method according to claim 8, wherein the first fluorochrome staining all sperm cells is used in a total concentration of about 50 nanomolar.

10. The method according to claim 1, wherein the staining of the sperm cells is performed at a temperature below 35° C.

11. The method according to claim 10, wherein the staining of the sperm cells is performed at a temperature of at the most 30° C.

12. The method according to claim 11, wherein the staining of the sperm cells is performed at a temperature between 15° C. and 25° C.

13. The method according to claim 12, wherein the staining of the cells is performed at room temperature.

14. The method according to claim 1, further comprising combining the sample or a subsample subsample is combined with an internal concentration standard means, and the determination of the absolute concentration of the sperm cells and the proportion of live sperm cells are performed simultaneously by means of a detection means responsive to the selective staining and to the internal concentration standard means.

15. The method according to claim 14, wherein the internal concentration standard means is constituted by standardization particles, the standardization particles being added in a predetermined number per weight or volume amount of the sample or subsample.

16. The method according to claim 14, wherein the standardization particles are fluorescent particles having a fluorescent quality distinguishable from the fluorescent qualities of the live sperm cells, dead sperm cells, and dying sperm cells.

17. The method according to claim 14, wherein the detection means comprises a flow cytometer.

18. The method according to claim 14, wherein the detection means comprises a laser scanning cytometer.

19. The method according to claim 15, wherein the size and absolute concentration of sperm cells of the subsample are adapted so that the number of sperm cells corresponds to between one tenth and ten times the number of standardization particles.

20. The method according to claim 19, wherein the size and absolute concentration of sperm cells of the subsample are adapted so that the number of sperm cells corresponds to between one quarter and four times the number of standardization particles.

21. The method according to claim 20, wherein the size and absolute concentration of sperm cells of the subsample are adapted so that the number of sperm cells corresponds to between half and twice the number of standardization particles.

22. The method according to claim 2, wherein the diluent is a diluent containing protein.

23. The method according to claim 22, wherein the protein is bovine serum albumin.

24. The method according to claim 1, wherein the determination of the absolute concentration of the sperm cells and the proportion of live sperm cells are determined as a mean value of the determination of the absolute concentration of the sperm cells and the proportion of live sperm cells performed on two or more subsamples of a semen sample.

25. The method for predicting the likelihood of fertilizing a female animal by artificial insemination with an insemination dose, comprising determining the absolute concentration of sperm cells in the semen sample from which the insemination dose is taken or is to be taken, and the proportion of live sperm cells therein by a method according to claim 1, and including the thus determined absolute concentration of the sperm cells in the semen sample and the proportion of live sperm cells therein, or the concentration, calculable therefrom, of live sperm cells in the sample, on the basis of which the likelihood of fertilizing the animal is predicted.

26. The method according to claim 25, wherein the likelihood of fertilizing the female animal is predicted on the basis of the determined absolute concentration of the sperm cells in the semen sample and the proportion of live sperm cells therein, or the concentration, calculable therefrom, of live sperm cells in the sample.

27. The method according to claim 25, wherein the prediction of the likelihood of fertilizing the female animal is performed on the basis of statistically significant correlations between fertility data obtained in insemination experiments with several female animals and data indicating one or more of the following: the absolute concentration of the sperm cells in the semen sample used in the insemination experiments the proportion of live sperm cells therein, or data indicating the concentration of live sperm cells therein.

28. The method according to claim 25, wherein the female animal is a multiparous animal, and the number of offspring resulting from the fertilization is also predicted.

29. The method according to claim 25, wherein the semen sample is a fresh ejaculate.

30. The method according to claim 25, wherein the semen sample is a frozen insemination dose, the sample being thawed before being subjected to the determination method.

31. The method according to claim 30, wherein data obtained by the determination method performed on the fresh ejaculate from which the insemination dose was taken are included together with data obtained by the determination method performed on the insemination dose.

32. The method for artificial insemination of a female animal, comprising predicting the likelihood of fertilizing a female animal, the prediction comprising determining the absolute concentration of sperm cells in the semen sample from which the insemination dose is taken or is to be taken, and the proportion of live sperm cells therein by a method according to claim 1, and including the thus determined absolute concentration of the sperm cells in the semen sample and the proportion of live sperm cells therein, or the concentration, calculable therefrom, of live sperm cells in the sample on the basis of which the likelihood of fertilizing the animal is predicted, and on basis of the predicted likelihood selecting an insemination dose for use with artificial insemination of the female animal.

33. The method according to claim 32, wherein the female animal is a multiparous animal, and the insemination dose is an insemination dose having a predicted likelihood of resulting in a number of offspring above a predetermined discrimination number.

34. The method according to claim 32, wherein the likelihood of fertilizing the female animal is predicted on the basis of the determined absolute concentration of the sperm cells in the semen sample and the proportion of live sperm cells therein, or the concentration, calculable therefrom, of live sperm cells in the sample.

35. The method according to claim 32, wherein the prediction of the likelihood of fertilizing the female animal is performed on the basis of statistically significant correlations between fertility data obtained in insemination experiments with several female animals and data indicating one or more of the following: the absolute concentration of the sperm cells in the semen sample used in the insemination experiments, the proportion of live sperm cells therein, or data indicating the concentration of live sperm cells therein.

36. The method according to claim 32, wherein the semen sample is a fresh ejaculate.

37. The method according to claim 32, wherein the semen sample is a frozen insemination dose, the sample being thawed before being subjected to the determination method.

38. The method according to claim 1, wherein the semen sample is a diluted subsample of said semen sample.

* * * * *

UNITED STATES PATENT AND TRADEMARK OFFICE
CERTIFICATE OF CORRECTION

| | | |
|---|---|---|
| PATENT NO. | : 7,070,917 B1 | Page 1 of 1 |
| APPLICATION NO. | : 09/914765 | |
| DATED | : July 4, 2006 | |
| INVENTOR(S) | : Preben Christensen and Jens Peter Stenvang | |

It is certified that error appears in the above-identified patent and that said Letters Patent is hereby corrected as shown below:

Col. 21 in claim 14, lines 54-55, delete "subsample is combined"

Col. 22 in claim 25, line 41, insert --in the parameters-- after "sample,"

Col. 22 in claim 27, line 58, please insert a comma between "experiments" and "the proportion"

Col. 23 in claim 32, line 16, insert --, in the parameters-- after "sample"

Col. 23 in claim 32, line 17, insert --, in the parameters-- after "predicted, and"

Col. 23 in claim 32, line 17, insert --the-- between "on" and "basis"

Signed and Sealed this

Thirty-first Day of July, 2007

JON W. DUDAS
*Director of the United States Patent and Trademark Office*